United States Patent [19]

Cannata et al.

[11] Patent Number: 5,107,013

[45] Date of Patent: Apr. 21, 1992

[54] PROCESS FOR THE DEBROMINATION OF 2-SUBSTITUTED-5-BROMO-6-METHOXYNAPHTHALENES

[75] Inventors: Vincenzo Cannata, Borgo Nuovo Pontecchio Marconi; Claudio Calzolari, Casalecchio di Reno; Giancarlo Tamerlani, Castel di Casio, all of Italy

[73] Assignee: Alfa Wassermann S.p.A., Pescara, Italy

[21] Appl. No.: 634,742

[22] Filed: Dec. 27, 1990

[30] Foreign Application Priority Data

Feb. 8, 1990 [IT] Italy .................. 19299 A/90

[51] Int. Cl.$^5$ .................. C07C 49/788; C07C 53/136; C07C 69/616; C07C 255/33
[52] U.S. Cl. ...................... 558/410; 560/56; 562/466; 564/173; 568/328
[58] Field of Search .................. 568/328; 562/466; 560/56; 558/410; 564/173

[56] References Cited

PUBLICATIONS

March, Advanced Organic Chemistry, 3rd Ed., (1985), p. 510.

*Primary Examiner*—Joseph Paul Brust
*Attorney, Agent, or Firm*—Bucknam and Archer

[57] ABSTRACT

Naphthalenes of formula

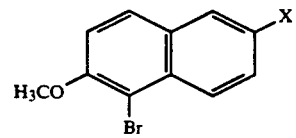

wherein X represents $COCH_3$, $COC_2H_5$, $CH(CH_3)COOH$, $CH(CH_3)COOR$, $CH(CH_3)CN$ and $CH(CH_3)CONHR_1$, R represents alkyl and $R_1$ represents hydrogen, alkyl or hydroxyalkyl, are debrominated by means of acceptors of bromine, like alkylarenes and alkoxyarenes, in the presence of Lewis acids.

5 Claims, No Drawings

PROCESS FOR THE DEBROMINATION OF 2-SUBSTITUTED-5-BROMO-6-METHOXYNAPHTHALENES

DISCLOSURE OF THE INVENTION

The object of the present invention is a process for the debromination of naphthalenes of formula

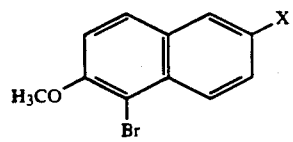
(I)

wherein X is a substituent selected from the group made by acetyl, propionyl, 1-carboxyethyl, 1-alkoxycarbonylethyl, 1-cyanoethyl, 1-aminocarbonylethyl, the nitrogen atom of this latter group optionally being substituted by alkyl or hydroxyalkyl groups.

The compounds obtained by debromination of the bromonaphthalenes of formula I represent many intermediates for the preparation of the 2-(6-methoxy-2-naphthyl)propionic acid of formula

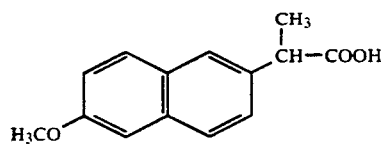
(II)

whose dextro-rotatory enantiomer is a widely used antiinflammatory drug, known as naproxen. When X represents CH(CH₃)COOH the debromination directly brings to the acid of formula II or to its enantiomer.

Many ways for the synthesis of naproxen are known: we will cite U.S. Pat. Nos. 3,896,157; 3,637,767; 3,658,858; 3,959,364; German Patent 2,646,792; Italian Patent Applications 20378 A/79; 20817 A/80; 24045 A/80; European Patent 35305.

In almost all these syntheses, the 2-acetyl-6-methoxynaphthalene (III, wherein R=CH₃) or the 2-propionyl-6-methoxynaphthalene (III, wherein R=C₂H₅) of formula

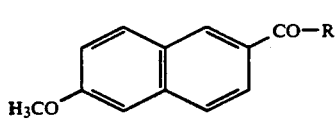
(III)

are the starting intermediates.

Both these ketones can be prepared by means of a Friedel-Crafts acylation of the 2-methoxynaphthalene. However, Haworth R. D. and Sheldrick G. (J.C.S. 1934, 864) already showed that this acylation gave to 1-acyl-2-methoxynaphthalenes when carried out in solvents like benzene or CS₂, while the desired isomers of formula III were obtained only by using nitrobenzene as solvent. Robinson R. and Rydon H. N. made the same verification (J.C.S. 1939, 1394), while Gupta B. P. and Haksar C. N. more recently [Agr. Univ. J. Res. 11, 2 (1962)] found the possibility to get the 2-acetyl-6-methoxynaphthalene with high yields by acylating the 2-methoxynaphthalene with acetic acid in a strong excess (10:1) of polyphosphoric acid.

It is evident that both the use of nitrobenzene (toxic and dangerous to handle, at least in great amounts) and the use of the polyphosphoric acid (whose discharge, mainly in great amounts, gives the well known drawbacks of entrophy) is not advisable for the industrial production.

A synthetic pathway, object of Italian Patent 1,168,387, wherein the 1-bromo-2-methoxynaphthalene is the starting compound, turned out to be competitive with this process.

By acetylation in methylene chloride according to Friedel-Crafts, this compound gives with high yields the corresponding 2-acetyl-5-bromo-6-methoxynaphthalene of formula

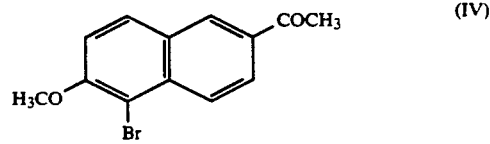
(IV)

from which it is possible to proceed according to the scheme reported hereinbelow

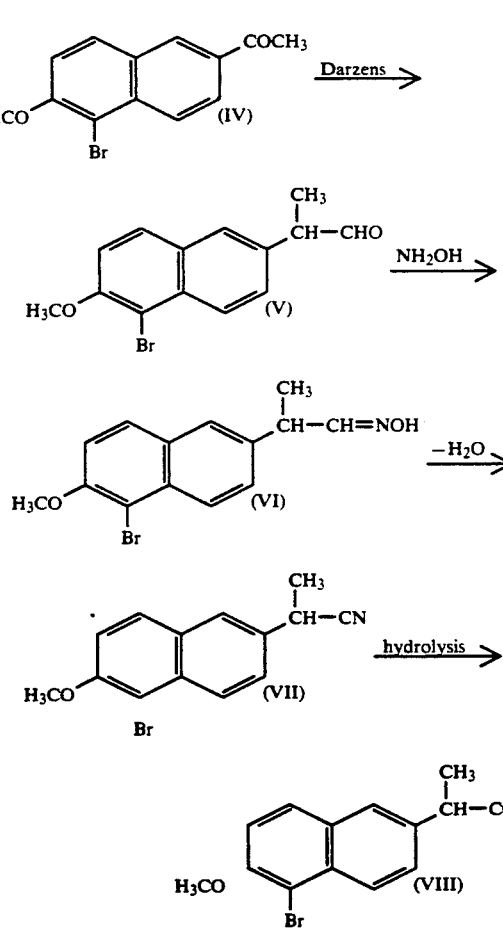

The (±)-2-(5-bromo-6-methoxy-2-naphthyl)propionic acid of formula VIII can then be transformed into naproxen or by debromination and subsequent resolution of the enantiomers, or by resolution and subsequent debromination of the (±)-2-(5-bromo-6-methoxy-2-naphthyl)propionic acid. For instance, the resolution can be carried out through the formation of diastereomer salts with (−)-N-methylglucamine, according to the already cited Italian Patent 1,168,387, or through the formation of diastereomer amides with optically active aminoalcohols (in particular one of the two enantiomers of the 2-aminobutanol)

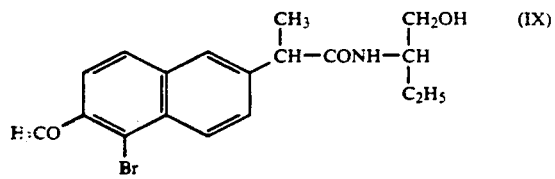

The debromination of the brominated acids (enantiomers or racemates) which are in the above summarized pathway of synthesis, is carried out, according to the methods known until now, by means of a reduction with $NaBH_4$ in the presence of palladium, or with nickel and hydrazine. The first method involves substantial expenses, firstly due to the use of great amounts of $NaBH_4$, in a minor but not negligible way to the unavoidable mechanical losses of palladium and to the cost of regeneration of the exhausted palladium. The process based on the use of nickel and hydrazine is much less costly: but nickel presents the well known problems of storage (the user falls within the "high hazard" class above certain amounts), while hydrazine is rightly considered toxic and dangerous, so that the maximum allowed threshold of revealable hydrazine in the environment is 0.1 ppm according to the safety rules.

Now we have found that the above mentioned compounds of formula I can be debrominated in an easy manner, much less costly than the previous processes and by using non-dangerous reagents, by treating the same compounds by means of acceptors of bromine in the presence of Lewis acids. The arenes activated towards the electrophylic reactions, for instance alkylarenes like toluene, m-xylene, mesitylene, durene etc., or alkoxyarenes like anisole showed to be particularly suitable as acceptors of bromine.

All the compounds normally used as catalysts in the Friedel-Crafts reactions, like $AlCl_3$, $FeCl_3$, $ZnCl_2$, $TiCl_4$ can be used as Lewis acids, even if the aluminum chloride showed to be particularly useful.

The molar ratio among the compounds of formula I, the acceptor of bromine and the Lewis acid is generally comprised between 1:1:1 and 1:2:2. Preferably about 1.5 moles of acceptor and about 1.5 moles of Lewis acid for each mole of the compounds of formula I are used.

Generally the reaction is carried out in a solvent; also an excess of the compound used as acceptor of bromine can be used as solvent, but the use of low-boiling halogenated hydrocarbons like methylene chloride, chloroform or 1,2-dichloroethane is preferred because of practical reasons. The temperature of the reaction can vary from about −20° C. and the boiling point of the reaction mixture; preferably the reaction is carried out between −10° C. and +30° C., practically at room temperature.

The yields of the reactions are generally quite high. Due to this fact, coupled with the easiness of execution and the above mentioned advantages of cost and lack of danger, the process according to the invention constitutes a remarkable technical progress.

European Patent 203,557 describes a process for the selective debromination of the (5-bromo-6-methoxy-2-naphthyl)-(1-bromoethyl)ketone or of its ketals in the presence of acceptors of bromine and of hydrogen halides (the patent also claims the use of the hydrogen halides in combination with the Lewis acids, but does not give any example). This patent claims phenols, phenolethers and aromatic ketones as acceptors of bromine and points out to the fact that (6-methoxy-2-naphthyl-)ethyl-ketone can be used as aromatic ketone, according to the scheme hereinbelow:

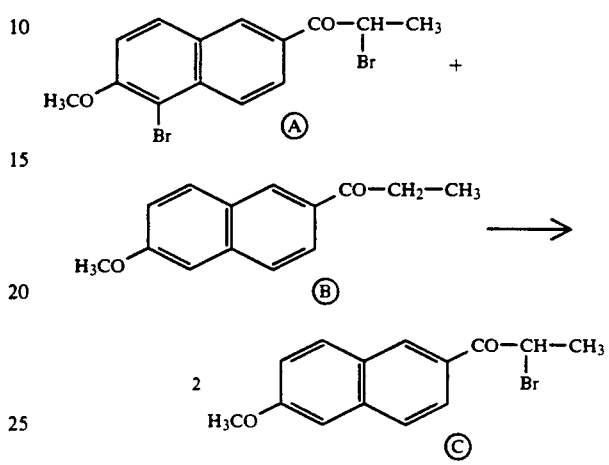

In other words, according to the above mentioned European Patent, the bromine in position 5 of the dibromoketone A goes to the position α of the propionyl residue of the compound B. This reaction is easily explained because of the activation of this position α to the carbonyl.

Therefore the fact that, in the process of debromination of the compounds of formula I according to the present invention, the transfer of bromine does not take place on the atom of carbon in the position α in respect of the activating group always present in the compounds themselves (either the group CO, or COOH, or COOR, or CN, or CONH—) has to be considered undoubtedly surprising.

In other words, the teaching of the European Patent 203557 would have discouraged from carrying out the process of the present invention.

The following examples show the here claimed process without limiting the extent.

EXAMPLE 1

2-acetyl-6-methoxynaphthalene a) 35.9 Grams of anhydrous aluminum chloride are suspended in 180 ml of anhydrous methylene chloride. The suspension is cooled to −10° C. and reacted first with 19.9 ml of acetyl chloride and then, in about 30 minutes, with a solution containing 58 g of 1-bromo-2-methoxy naphthalene in 140 ml of anhydrous methylene chloride, while keeping the temperature at −10° C. This temperature is kept for other 30 minutes obtaining a solution containing the 2-acetyl-5-bromo-6-methoxynaphthalene.

b) 8.2 Grams of anhydrous aluminum chloride and 59 ml of toluene are added to the solution of 2-acetyl-5-bromo-6-methoxynaphthalene obtained in example 1, keeping the temperature at −10° C. The reaction mixture is kept under stirring at room temperature for 20 hours and then it is slowly poured into a mixture made by 200 g of crushed ice and by 75 ml of a 35% (w/v) aqueous solution of hydrochloric acid.

The layers are separated, the aqueous phase is extracted with 30 ml of methylene chloride and then is discarded, while the organic phases are collected and washed twice with 100 ml of a 6N aqueous solution of hydrochloric acid and then with 50 ml of water. The organic layer is then added with 50 ml of water, the pH is brought to about 12 by adding a 30% (w/v) aqueous solution of sodium hydroxide and the aqueous phase is discarded.

The organic solution is dried over anhydrous sodium sulfate, evaporated to dryness under vacuum and the residue is crystallized by n-heptane obtaining 43.5 g of product, with a yield equal to 88.7% calculated on the basis of the starting material 1-bromo-2-methoxynaphthalene.

EXAMPLE 2

2-Acetyl-6-methoxynaphthalene

45 Ml of m-xylene are added in 15 minutes to the solution of 2-acetyl-5-bromo-6-methoxynaphthalene obtained as in example 1a) and then 8.2 g of anhydrous aluminum chloride are added, while keeping the temperature at $-10°$ C. The reaction mixture is kept for three hours under stirring at room temperature and then it is worked as in example 1 obtaining 42.5 g of product with a yield equal to 86.7% calculated on the basis of the starting material 1-bromo-6-methoxynaphthalene.

EXAMPLE 3

2-Acetyl-6-methoxynaphthalene 45.3 Ml of p-xylene and 8.2 g of anhydrous aluminum chloride are added to the solution of 2-acetyl-5-bromo-6-methoxynaphthalene obtained as in example 1a), while keeping the temperature at $-10°$ C. The reaction mixture is kept for 16 hours under stirring at room temperature and then it is worked as in example 1 obtaining 42.8 g of product with a yield equal to 87.3% calculated on the basis of the starting material 1-bromo-2-methoxynaphthalene.

EXAMPLE 4

2-Acetyl-6-methoxynaphthalene

51 Ml of mesitylene and 8.2 g of anhydrous aluminum chloride are added to the solution of 2-acetyl-5-bromo-6-methoxynaphthalene obtained as in example 1a), while keeping the temperature at $-10°$ C. The reaction mixture is kept for 3 hours under stirring at 0° C. and then it is worked as in example 1 obtaining 43.2 g of product with a yield equal to 88.2% calculated on the basis of the starting material 1-bromo-2-methoxynaphthalene.

EXAMPLE 5

2-Acetyl-6-methoxynaphthalene

57 Ml of tert-butylbenzene and 8.2 g of anhydrous aluminum chloride are added to the solution of 2-acetyl-5-bromo-6-methoxynaphthalene obtained as in example 1a), while keeping the temperature at $-10°$ C. The reaction mixture is kept for 16 hours under stirring at room temperature and then it is worked as in example 1 obtaining 41.8 g of product with a yield equal to 85.3% calculated on the basis of the starting material 1-bromo-2-methoxynaphthalene.

EXAMPLE 6

2-Acetyl-6-methoxynaphthalene

42 Ml of β-naphthol and 16.2 g of anhydrous aluminum chloride are added to the solution of 2-acetyl-5-bromo-6-methoxynaphthalene obtained as in example 1a), while keeping the temperature at $-10°$ C. The reaction mixture is kept for 48 hours under stirring at room temperature and then it is worked as in example 1 with the only difference that the product is crystallized by isopropyl alcohol. 19 Grams of product are obtained with a yield equal to 38.7% calculated on the basis of the starting material 1-bromo-2-methoxynaphthalene.

EXAMPLE 7

2-Acetyl-6-methoxynaphthalene

80 Ml of anisole and 18 g of anhydrous aluminum chloride are added to the solution of 2-acetyl-5-bromo-6-methoxynaphthalene obtained as in example 1a), while keeping the temperature at $-10°$ C. The reaction mixture is kept for 24 hours under stirring at room temperature and then it is worked as in example 1 obtaining 38.5 g of product with a yield equal to 78.5% calculated on the basis of the starting material 1-bromo-2-methoxynaphthalene.

EXAMPLE 8

2-Acetyl-6-methoxynaphthalene

48 Grams of naphthalene and 16.7 g of anhydrous aluminum chloride are added to the solution of 2-acetyl-5-bromo-6-methoxynaphthalene obtained as in example 1a), while keeping the temperature at $-10°$ C. The reaction mixture is kept under stirring for 2 hours at 0° C. and for 20 hours at room temperature and then it is worked as in example 1 obtaining 38.8 g of product with a yield equal to 79.2% calculated on the basis of the starting material 1-bromo-2-methoxynaphthalene.

EXAMPLE 9

2-Acetyl-6-methoxynaphthalene

30 Grams of anhydrous aluminum chloride are added portionwise to a mixture made of 41.85 g of 2-acetyl-5-bromo-6-methoxynaphthalene, 22.15 g of durene and 180 ml of anhydrous methylene chloride cooled to $-5°$ C., in such a manner that the temperature of 20° C. is not exceeded. The reaction mixture is kept for 2 hours at room temperature after the end of the addition and then it is worked as in example 1 obtaining 27.1 g of product with a yield equal to 90.6% calculated on the basis of the starting material 2-acetyl-5-bromo-6-methoxynaphthalene.

EXAMPLE 10

6-Methoxy-2-propionylnaphthalene 29.3 Grams of 5-bromo-6-methoxy-2-propionylnaphthalene are dissolved in 100 ml of anhydrous methylene chloride and in 20.8 ml of mesitylene. 20 Grams of anhydrous aluminum chloride are added portionwise to the reaction mixture cooled to $-5°$ C. under strong stirring, while keeping the temperature below 20° C. The reaction mixture is kept for over 3 hours under stirring at room temperature, then it is slowly poured under strong stirring into a mixture made of 110 g of ice and of 35 ml of a 35% (w/v) aqueous solution of hydrochloric acid. The layers are separated after 15 minutes of stirring and the aqueous layer is discarded. The organic layer first is twice washed with 50 ml of a 6N aqueous solution of hydrochloric acid and then with 50 ml of water. The organic solution is then added with 50 ml of water and the pH is brought to 12 by means of a 30% (w/v) aqueous solution of sodium hydroxide.

The aqueous phase is discarded while the organic phase is dried over anhydrous sodium sulfate and evaporated to dryness under vacuum. The residue is crystallized by n-heptane obtaining 20.2 g of product with a yield equal to 94.3%.

EXAMPLE 11

2-(6-Methoxy-2-naphthyl)propionitrile

10 Grams of anhydrous aluminum chloride are added portionwise and under stirring to a solution containing 14.5 g of 2-(5-bromo-6-methoxy-2-naphthyl)propionitrile dissolved in 60 ml of methylene chloride and 8.3 ml of mesitylene, while keeping the temperature at about 20° C. The reaction mixture is kept at this temperature under stirring for 1 hour and then is slowly poured into a mixture made of 60 g of crushed ice and of 20 ml of a 6N aqueous solution of hydrochloric acid. The layers are separated after 15 minutes of stirring and the aqueous layer is discarded. The organic layer is twice washed with 25 ml of a 6N aqueous solution of hydrochloric acid, then with 25 ml of water and is dried over anhydrous sodium sulfate. The organic solution is evaporated to dryness under vacuum and the residue is crystallized from tetrachloroethylene obtaining 7.5 g of product with a yield of 71%.

EXAMPLE 12

2-(6-Methoxy-2-naphthyl)propionamide 15.4 Grams of 2-(5-bromo-6-methoxy-2-naphthyl)propionamide are added to a mixture made of 60 ml of chloroform and 8.3 ml of mesitylene.

10 Grams of anhydrous aluminum chloride are added portionwise under stirring to the mixture cooled to 0° C., while keeping the temperature at about 20° C. The reaction mixture is kept under stirring at about 20° C. for 2 hours and then is worked as in example 11 obtaining 10.9 g of product with a yield equal to 95.1%.

EXAMPLE 13

2-(6-Methoxy-2-naphthyl)propionic acid, methyl ester 10.4 Ml of mesitylene are added to a solution containing 16.1 g of the methyl ester of the 2-(5-bromo-6-methoxy-2-naphthyl)propionic acid dissolved in 65 ml of methylene chloride.

13.5 Grams of anhydrous aluminum chloride are added portionwise under stirring to the reaction mixture cooled to −5° C., while keeping the temperature at about 15° C. The reaction mixture is kept under stirring at about 15° C. for 2 hours and then is poured into a mixture made of 68 g of crushed ice and 15 ml of a 35% (w/v) aqueous solution of hydrochloric acid. The layers are separated, the aqueous layer is extracted with 30 ml of methylene chloride and then is discarded. The organic layers are collected, first washed with 50 ml of a 1N aqueous solution of hydrochloric acid, then with 50 ml of water and lastly with 50 ml of a 8% (w/v) aqueous solution of sodium bicarbonate. The organic solution is then dried over anhydrous sodium sulfate and concentrated to dryness under vacuum. The residue is crystallized from n-hexane obtaining 10.6 g of product with a yield equal to 86.7%.

EXAMPLE 14

2-(6-Methoxy-2-naphthyl)propionic acid, methyl ester 16.1 Grams of the methyl ester of the 2-(5-bromo-6-methoxy-2-naphthyl)propionic acid are dissolved in 65 ml of methylene chloride and then 10.4 ml of mesitylene and 12 ml of anhydrous titanium tetrachloride are added while keeping the temperature at about 20° C. The reaction mixture is kept under stirring at room temperature for 80 hours and then is poured into a mixture made of 68 g of crushed ice and of 15 ml of a 35% (w/v) aqueous solution of hydrochloric acid. The layers are separated after 15 minutes of stirring, the aqueous layer is extracted with 30 ml of methylene chloride and then is discarded. The organic layers are collected, first washed with 50 ml of a 1N aqueous solution of hydrochloric acid, then with 50 ml of water and lastly with 50 ml of a 8% (w/v) aqueous solution of sodium bicarbonate. The organic solution is dried over anhydrous sodium sulfate and then is evaporated under vacuum. The residue is crystallized first with n-hexane and then with methyl alcohol obtaining 4 g of product with a yield equal to 32.7%.

EXAMPLE 15 d-2-(6-Methoxy-2-naphthyl)propionic acid, methyl ester 20.8 Ml of mesitylene are added to a solution of 32.3 g of the methyl ester of the d-2-(6-methoxy-2-naphthyl)propionic acid dissolved in 130 ml of methylene chloride. 20 Grams of anhydrous aluminum chloride are added portionwise under stirring to the reaction mixture cooled to −5° C., while keeping the temperature at about 10° C. The reaction mixture is kept under stirring for one hour at about 10° C. and then is poured into a mixture made of 100 g of crushed ice and of 15 ml of a 35% (w/v) aqueous solution of hydrochloric acid. The layers are separated after 15 minutes of stirring, the aqueous phase is discarded while the organic layer is twice washed with 100 ml of a 1N aqueous solution of hydrochloric acid, once with 100 ml of water and once with 100 ml of a 8% (w/v) aqueous solution of sodium bicarbonate. The organic solution is dried over anhydrous sodium sulfate and concentrated to dryness under vacuum. The residue is crystallized by n-hexane obtaining 22.8 g of pure product having $[\alpha]_D^{20} = +80.3°$ (C=1% in chloroform) with a yield equal to 93.3%.

EXAMPLE 16

α-2-(6-Methoxy-2-naphthyl)-N-[α-2-(1-hydroxy)-butyl]propionamide 20.8 Ml (0.15 moles) of mesitylene and 38 g (0.1 moles) of α-2-(5-bromo-6-methoxy-2-naphthyl)-N-[α-2-(1-hydroxy)-butyl]propionamide are added to 200 ml of methylene chloride. The mixture is cooled to −3° C. and 20 g (0.15 moles) of anhydrous aluminum chloride are added portionwise in such a manner that the temperature does not exceed 20° C. The reaction mixture is kept one hour under stirring at 20° C. and then is poured under stirring into a mixture made of 120 g of ice and 10 ml of 32% hydrochloric acid. The layers are separated after having added further 100 ml of methylene chloride and heated to 35° C. The organic layer is washed with 10 ml of hydrochloric acid and then with water and lastly is concentrated under vacuum in a rotating evaporator. The residue is added with 150 ml of toluene, heated to the boiling, cooled, filtered and dried obtaining 28 g of α-2-(6-methoxy-2-naphthyl)-N-[α-2-(1-hydroxy)-butyl]propionamide with a yield of 95.7%.

EXAMPLE 17 d-2-(6-Methoxy-2-naphthyl)propionic acid 20.8 Ml (0.15 moles) of mesitylene and 30.9 g (0.10 moles) of (+)-2-(5-bromo-6-methoxy-2-naphthyl)propionic acid are added to 150 ml of chloroform and the mixture is cooled to 0° C. 20 Grams (0.15 moles) of anhydrous aluminum chloride are added portionwise under strong stirring to the mixture while going on with the cooling so that temperature does not exceed 20° C. The reaction mixture is kept at this temperature for 3 hours and then is poured into a mixture made of 100 g of ice and 10 ml of 32% hydrochloric acid. The reaction mixture is heated to 45° C., the layers are separated, the organic layer is twice washed with 50 ml of 1M hydrochloric acid and then with 100 ml of water. The organic layer is concentrated under vacuum and the residue is crystallized from 75 ml of toluene. The product is filtered and dried obtaining 21 g of the title compound, which corresponds to the drug known as naproxen, having $[\alpha]_D^{20} = +66.5°$ (C=1% in chloroform), with a yield of 91%.

We claim:

1. A process for the debromination of 2-substituted-5-bromo-6-methoxynaphthalenes of formula

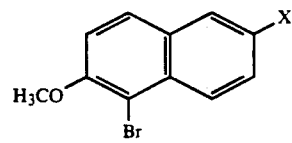

wherein X is a member selected from the group consisting of acetyl, propionyl, 1-carboxyethyl, 1-alkoxycarbonylethyl, 1-cyanoethyl, and 1-aminocarbonylethyl wherein the nitrogen atom of the amino group is unsubstituted or substituted by alkyl or hydroxyalkyl, which consists of reacting said compound of formula I with an acceptor of bromine in the presence of a Lewis acid, said acceptor of bromine being an unsubstituted arene, an alkylarene, B-naphthol or an alkoxyarene in a solvent which is a low boiling halogenated hydrocarbon or an excess of the same compound used as the acceptor of bromine at a temperature between −20° C. and the boiling point of the reaction mixture in a molar ratio between said compound of formula I, said acceptor of bromine and said Lewis acid between 1:1:1 and 1:2:2.

2. The process according to claim 1 wherein said Lewis acid is aluminum chloride, ferric chloride, zinc chloride or titanium tetrachloride.

3. The process according to claim 1 wherein said alkylarene is toluene, xylene, mesitylene, durene or tert-butyl benzene.

4. The process according to claim 1 wherein said alkoxyarene is anisole.

5. The process according to claim 1 wherein said low boiling halogenated hydrocarbon is methylene chloride, chloroform, or 1, 2-dichloroethane.

* * * * *